US00PP21432P2

(12) United States Plant Patent
Pinochet

(10) Patent No.: US PP21,432 P2
(45) Date of Patent: Nov. 2, 2010

(54) **VARIETY OF *PRUNUS* ROOTSTOCK NAMED 'PURPLEPAC'**

(50) Latin Name: *(Prunus dulcis×P. persica)×(P. persica×P. davidiana)*
Varietal Denomination: Purplepac

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 0 days.

(21) Appl. No.: 12/455,208

(22) Filed: May 29, 2009

(51) Int. Cl.
*A01H 5/00* (2006.01)

(52) U.S. Cl. ..... Plt./183

(58) Field of Classification Search ..... Plt./183
See application file for complete search history.

*Primary Examiner*—Susan B McCormick Ewoldt
(74) *Attorney, Agent, or Firm*—The Webb Law Firm

(57) ABSTRACT

A new and distinct hybrid peach-almond plant used as a rootstock that exhibits root-knot nematode resistance, red leaves, and compatibility with peach, nectarine, almond, and plum varieties.

5 Drawing Sheets

Botanical classification: [(*Prunus dulcis×P. persica*)×(*P. persica×P. davidiana*)].
Varietal denomination: 'Purplepac'.

BACKGROUND OF THE INVENTION

The present invention comprises a new and distinct cultivar of peach-almond hybrid [(*Prunus dulcis×P. persica*)×(*P. persica×P. davidiana*)] used as a rootstock known by the varietal name 'Purplepac'. The new variety was discovered in Barcelona, Spain in 1999 as a result of a planned breeding program. The new variety is the result of a cross between 'Felinem' (*Prunus dulcis×P. persica*) (female parent, unpatented) and 'Cadaman' (*Prunus persica×P. davidiana*). The purpose of the breeding program was to develop rootstocks that are adaptive to Mediterranean conditions, with medium vigor, low chilling requirements, a tolerance to calcareous soils, and good productivity. The new variety exhibits similar good tolerance to calcareous soils, moderate root-knot nematode resistance, and low chilling requirements to both parents, but differs from both parents in its anticipation of fruit maturation, lower tree vigor, and the fact that it tolerates waterlogging conditions better. Further, the new variety has similar peach-like leaves, productivity, and root-knot nematode resistance to 'Nemaguard' (*Prunus persica×P. davidiana*) (unpatented), but differs from 'Nemaguard' in its red leaves, tolerance to iron chlorosis, and its ability to withstand wet and heavily textured soils better. The new variety has been trial and field tested and has been found to retain its distinctive characteristics and remain true to type through successive propagations. The following characteristics distinguish 'Purplepac' from other varieties known to the breeder:

1. Red leaves;
2. Peach-like leaves;
3. No suckering;
4. Better tolerance to alkaline soils and salinity than most peach rootstocks;
5. Better tolerance to wet soil conditions than most peach rootstocks;
6. Moderate resistance to root-knot nematodes (*Meloidogyne* spp.);

7. Induces early fruit maturation in peach varieties;
8. Induces large-sized fruits; and
9. Low chilling requirements.

DESCRIPTION OF THE DRAWINGS

The accompanying photographic drawings illustrate the new variety with the color being as nearly true as is possible with color illustrations of this type.

DESCRIPTION OF THE PLANT

Figure 1:
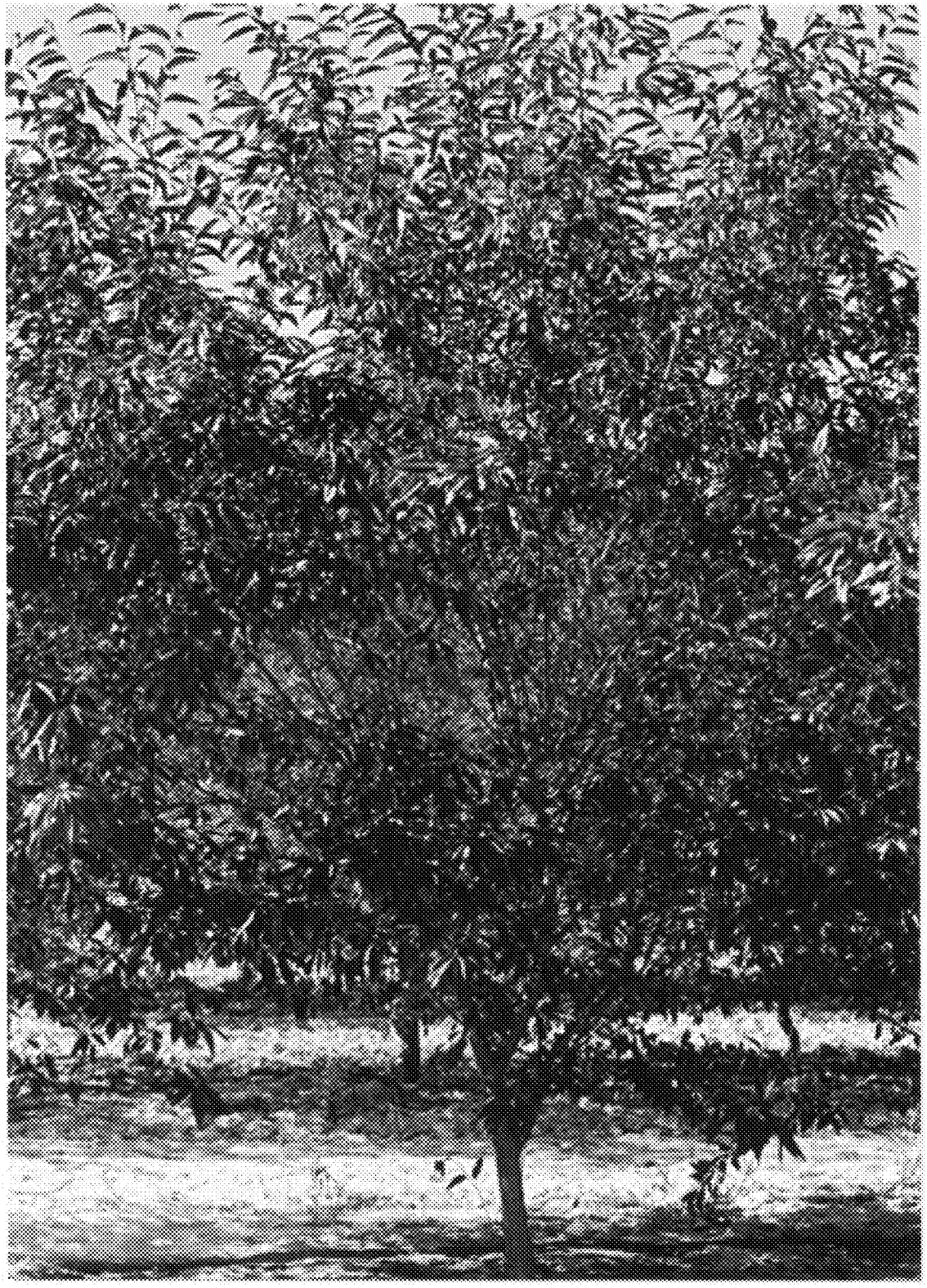
FIG. 1 shows an entire tree of the new variety.
Figure 2:
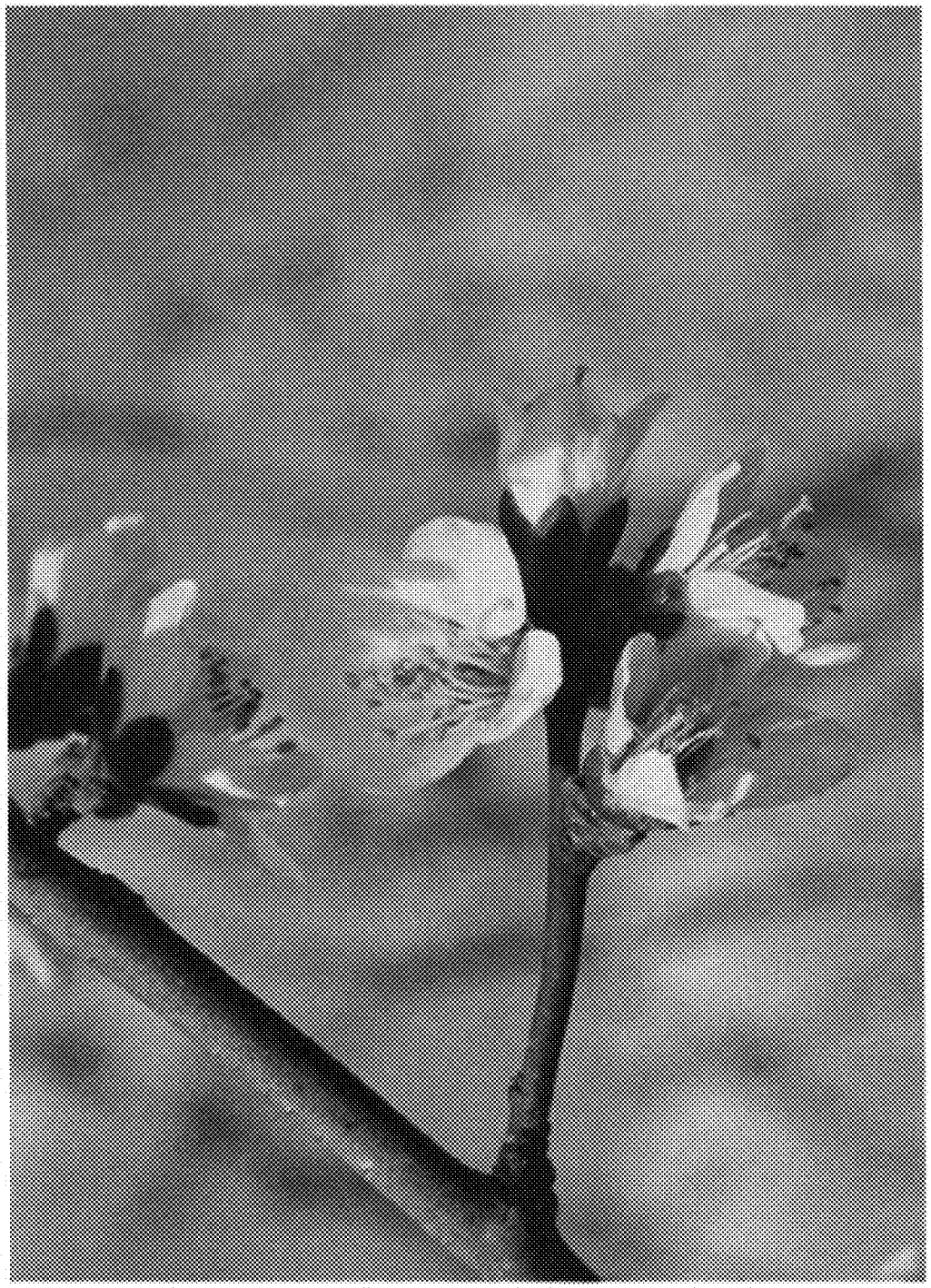
FIG. 2 shows the flowers of the new variety.
Figure 3:
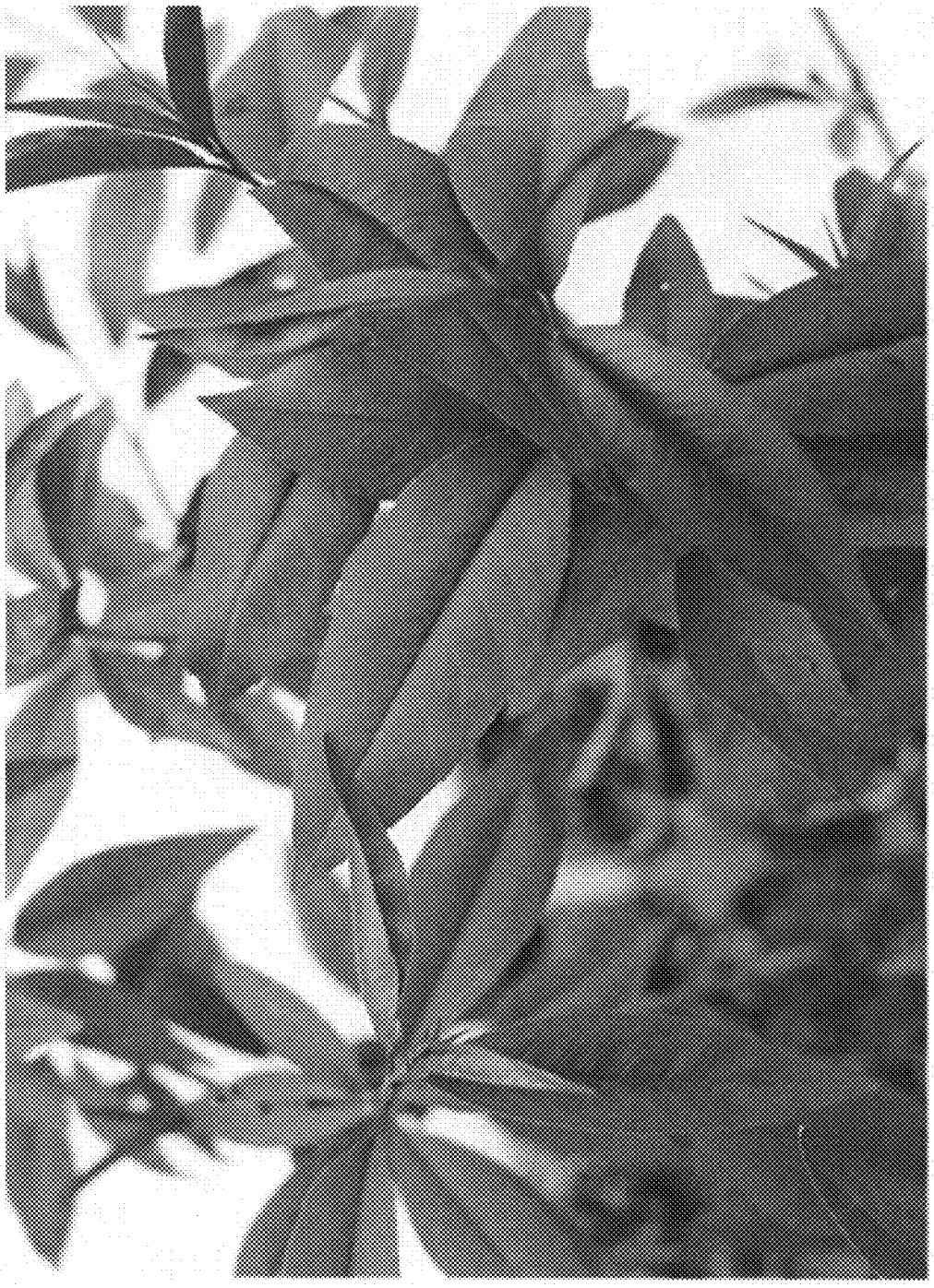
FIG. 3 shows the leaves of the new variety.
Figure 4:
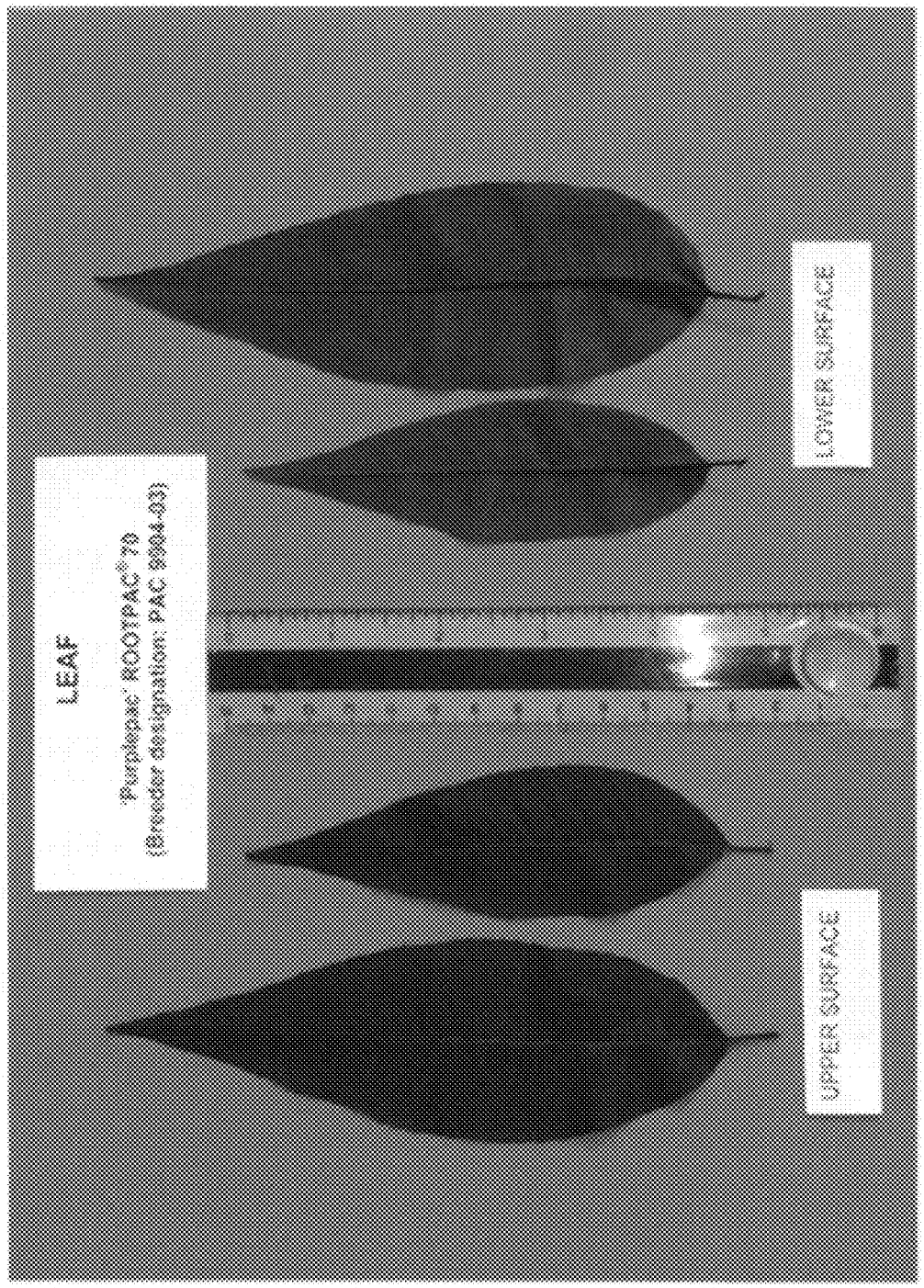
FIG. 4 shows the upper and lower surface of a young and mature leaf of the new variety.
Figure 5:
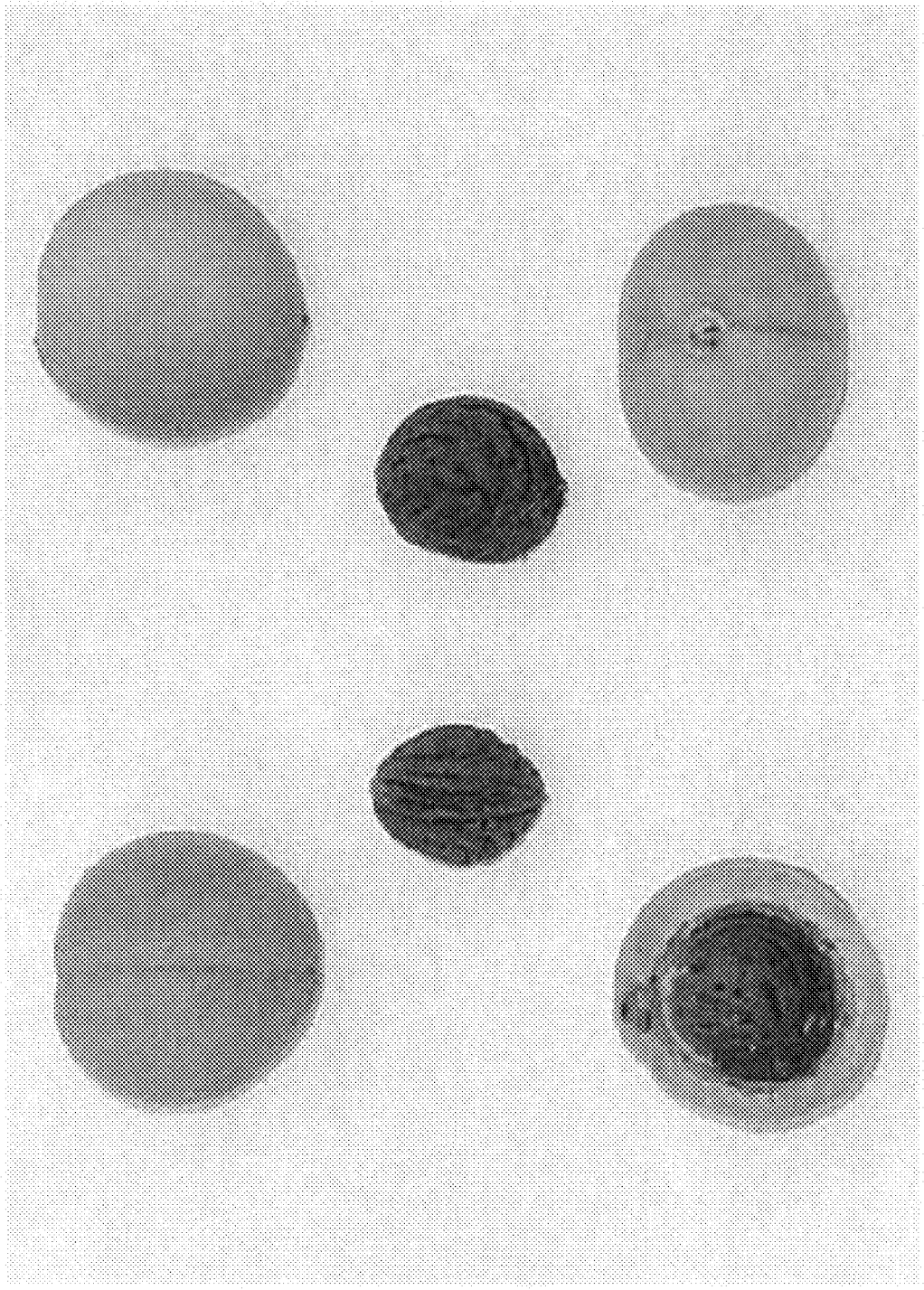
FIG. 5 shows the fruit of the new variety.

The following detailed description sets forth the characteristics of the new cultivar. The data which defines these characteristics was collected under natural daylight on plants produced by asexual reproductions via in vitro propagation carried out in Barcelona, Spain. The plants were grown under normal field conditions with drip irrigation, as well as in 5 and 40 liter containers. Color designations are presented with reference to the "Dictionary of Color" by A. Maerz and M. Rea Paul, Second Edition (1950).

TREE

Age: 8 years.
Size: 3.2 meters tall.
Vigor: Medium-high.
Density: Low to medium.
Form: Compact.
Production: Abundant.
Growth type: Upright.
Bearing: Fruit bearing.
Pathogen resistance:
*Fungal disease.*—Unknown.
*Insects.*—Unknown.
*Mites.*—Unknown.

*Viruses.*—Unknown.

*Other diseases.*—Root-knot nematodes (*Meloidogyne* spp.).

Rootstock performance:

*Root sprouts* (*suckering*).—Not present.

*Anchorage.*—Good with a big root system.

*Compatibility.*—Compatible with peach, nectarine, almond, and plum varieties.

*Vigor:.*—Medium-high (10-15% less than 'Nemaguard').

Trunk:

*Size.*—Fairly large; cylindrical and from 16 to 17 cm. in diameter.

*Surface texture.*—Smooth with large, horizontal lenticels.

*Bark color.*—Plate 13, A 2 (Piping Rock, Grey Stone) as the predominant color with some slight reddish-brown tones.

*Lenticels.*—Length: 5 mm. to 3 cm. Width: 2 to 3 mm. Color: Plate 14, B 2 (Sirocco). Density: Medium.

Branches:

*Diameter.*—Variable; from 1 to 2.5 cm. in the same growing season.

*Surface texture.*—Smooth in the current season with scarfskin as maturity advances.

*Color.*—Plate 15, C 3 (Métallique).

*Form.*—Circular in diameter.

*Average angle.*—Acute.

*Bud arrangement.*—Helicoidal throughout the branch.

*Lenticels.*—Length: 1 to 2 mm. in the first year of growth; 2 to 4 mm. after the second year of growth. Width: 0.5 to 1 mm. Shape: Elongated horizontally. Density: Low. Color: Plate 15, A 1.

Leaves:

*Length.*—12 to 15 cm.

*Width.*—4 to 6 cm.

*Form.*—Lanceolate.

*Texture.*—Smooth.

*Thickness.*—Thin.

*Base.*—Acute.

*Apex.*—Acute.

*Margin.*—Crenate, but turning serrate as the leaves mature.

*Pubescence.*—Upper surface: Absent. Lower surface: Absent.

*Color.*—Young leaves: Upper surface: Plate 8, J 7 (Liberia). Lower surface: Plate 8, L 7 (Carbuncle). Mature leaves: Upper surface: Plate 8, H 2; In May, turning to greener tones in the season. Lower surface: Plate 8, E 4.

*Petiole.*—Shape: Straight to slightly curved backwards with a central groove along the upper side with 1 or 2 very small sized nectaries near the base of the leaf. Length: 10 to 20 mm. Diameter: 1 to 2 mm. Color: Plate 8, L 6 (Mirador, Argentina, Art Brown).

*Veins.*—Venation type: Tree type disposition. Color: Upper surface: Plate 8, L 8 (Brazil Brown). Lower surface: Plate 7, J 6 (Garnet, Spanish Wine, Pigeon Blood).

Flower buds:

*Pedicel.*—Length: 1 mm. Diameter: 1 mm. Color: Plate 8, L 9 (Maracaibo, Domingo Brown).

*Bud.*—Length: 4 to 5 mm. Width: 3 to 4 mm. Shape: Ovoid to round. Color: Plate 7, H 7 (Cedar).

Flowers:

*Bloom timing.*—February 18th in Barcelona, Spain.

*Blooming period.*—10 to 15 days.

*Pollination requirements.*—None.

*Number of flowers per raceme.*—Normally individual, occasionally 2 present.

*Fragrance.*—Rose-like.

*Petals.*—Number: 5. Length: 12 to 16 mm. Width: 12 to 14 mm. Shape: Rounded. Aspect: Cupped upwards and inwards and slightly overlapping. Margin: Even with a slight indentation at the upper edge. Texture and appearance: Smooth.

*Color.*—When opening: Upper surface: Plate 2, B 1. Lower surface: Plate 2, C 1. Fully opened: Upper surface: Plate 1, C 2 (Peach Blossom). Lower surface: Plate 1, C 1.

*Sepals.*—Shape: Elliptic. Margin: Smooth. Texture: Pubescent at the edges. Length: 8 to 10 mm. Width: 3 to 5 mm. Color: Upper surface: Plate 7, L 7 (Maroon). Lower surface: Plate 6, L 6 (Chianti, Antique Ruby).

*Stamens.*—Number (per flower): 15 to 20. Filament length: 9 to 12 mm.

*Anthers.*—Shape: Kidney-shaped. Length: 1.5 to 2 mm. Color: Plate 12, E 7 (Cinnamon).

*Pollen.*—Color: Plate 13, K 8 (Centennial Brown). Amount: Abundant.

*Pistils.*—Length: 12 to 17 mm.

*Style.*—Length: 11 to 14 mm. Color: Plate 2, I 3.

*Stigma.*—Shape: Rounded. Color: Plate 19, I 1 (Butterfly).

Fruit description:

*Size.*—Small.

*Diameter.*—2 to 3.5 cm.

*Length.*—3 to 3.5 cm.

*Skin.*—Thickness: Thin. Texture: Pubescent. Tendency to crack: Low. Color: Plate 11, L 1 (Chartreuse) to Plate 10, I 2. Ground color: Variable in shades.

*Flesh.*—Aroma: Very weak. Color: Plate 11, E 5 (Raffia) . Texture: Semi-hard. Eating quality: Leathery.

*Seeds.*—Number per fruit: One. Length: 1.9 to 2.3 cm. Breadth: 1.3 to 1.6 cm. Form: Wide and elliptic. Color: Plate 7, J 8 (Domingo).

*Stem.*—Length: Variable, but can be long (20 cm. to 1 m.). Width: 3 to 8 mm. Color: Plate 8, E 5 (Chippendale, African Brown, Afghan) on early season's growth from April to June.

Use: As a rootstock for peach, nectarine, and almond varieties.

Winter hardiness: Hardy (under the conditions in Spain).

Bud winter hardiness: Medium.

Drought tolerance: Moderately tolerant.

I claim:

1. A new and distinct variety of hybrid peach-almond plant, as illustrated and described herein.

* * * * *